United States Patent [19]
Mills et al.

[11] Patent Number: 5,464,024
[45] Date of Patent: Nov. 7, 1995

[54] REUSABLE SURGICAL DRAPE WITH FLUID-RETAINING TROUGH

[75] Inventors: Veronica A. Mills, Cincinnati; Bonnie F. Fazio, Morrow, both of Ohio

[73] Assignee: Standard Textile Co., Inc., Cincinnati, Ohio

[21] Appl. No.: 270,366

[22] Filed: Jul. 5, 1994

[51] Int. Cl.[6] .................................. A61C 19/08
[52] U.S. Cl. ........................... 128/849; 128/853
[58] Field of Search ........................ 128/849–856

[56] References Cited

U.S. PATENT DOCUMENTS

| | | | |
|---|---|---|---|
| 3,882,859 | 5/1975 | Ericson | 128/854 |
| 4,089,331 | 5/1978 | Hartigan et al. | 128/850 |
| 4,275,720 | 6/1981 | Wichman | 128/853 |
| 4,869,271 | 9/1989 | Idris | 128/853 |
| 4,890,628 | 1/1990 | Jackson | 128/849 |
| 5,038,798 | 8/1991 | Dowdy et al. | 128/849 |
| 5,143,091 | 9/1992 | Patnode et al. | 128/849 |
| 5,161,544 | 11/1992 | Morris | 128/849 |
| 5,209,243 | 5/1993 | Glassman | 128/849 |
| 5,222,507 | 6/1993 | Taylor | 128/849 |
| 5,335,677 | 8/1994 | Busch | 128/852 |
| 5,345,946 | 9/1994 | Butterworth et al. | 128/853 |
| 5,394,891 | 3/1995 | Mills et al. | 128/852 |
| 5,398,700 | 3/1995 | Mills et al. | 128/853 |

FOREIGN PATENT DOCUMENTS

| | | | |
|---|---|---|---|
| 0166124 | 1/1986 | European Pat. Off. | 128/854 |
| 2650501 | 2/1991 | France | 128/849 |

*Primary Examiner*—Robert A. Hafer
*Attorney, Agent, or Firm*—Frost & Jacobs

[57] ABSTRACT

A reusable surgical drape having a fenestration to be positioned at the surgical site and a trough for collecting liquids which flow from the surgical site. The trough comprises a substantially rectangular panel of liquid repellant fabric having rounded corners and having an opening formed therein corresponding to the drape fenestration. The trough-forming panel is sewn to the drape about the peripheries of their corresponding opening and fenestration. In one embodiment all four sides of the trough-forming panel are folded inwardly toward the fenestration to form liquid receiving and retaining trough segments about the drape fenestration. At each of the corners, where adjacent trough segments meet, the outer peripheral edge of the trough-forming panel is gathered, resulting in a continuous rectangular trough about the fenestration, having substantially rectilinear side segments and rounded corner segments free of seams, stitches, folds or multiple layers. Snaps are provided to maintain the shape of the trough segments. In another embodiment the structure is substantially the same except that only three sides of the trough-forming panel are folded inwardly to form trough segments with rounded gathered corners therebetween. The fourth side is sewn to the drape for a part of its length. Snaps are provided to fold and close those ends of those trough segments adjacent the unfolded fourth side of the trough-forming panel.

13 Claims, 4 Drawing Sheets

REUSABLE SURGICAL DRAPE WITH FLUID-RETAINING TROUGH

TECHNICAL FIELD

The invention relates to a reusable surgical drape, and more particularly to such a surgical drape having a fenestration with a three or four sided trough of liquid repellant material thereabout, the trough having between trough segments smooth, curved corners free of seams, stitches, folds and multiple folded layers.

BACKGROUND ART

As is well known in the art, there are a number of surgical procedures which are characterized by large quantities of fluid flowing from the surgical site. The fluid may constitute body fluid from the patient or irrigation fluid from irrigation apparatus. In either event, the fluid must be allowed to drain from the surgical site and, for the protection of both the patient and the operating staff, the fluid flow should be controlled by collection and containment. Where large quantities of fluid are involved, it may be further be necessary to drain the fluid from the collection and containment means.

Prior art workers have attempted to control and collect liquid from the operating site in numerous ways. For example, one way to collect and contain fluid from the operating site is to surround the site with absorptive towels or the like. It is also common practice to utilize suction and surgical sponges within the body cavity. None of these expedients is particularly successful when large quantities of liquid are involved. As a consequence, prior art workers have devised liquid collecting bags constituting a part of the surgical drape, itself. U.S. Pat. Nos. 4,890,628 and 5,002,069 are exemplary of such collection bags. In U.S. Pat. No. 4,890,628 the collection bag has, integral therewith, a pair of upstanding members which partially, at least, surround the site. These upstanding members tend to channel fluid into the collection bag. Both the upstanding members and the bag are provided with malleable inserts by which they may be shaped and maintained in the desired shape. The collection bag of U.S. Pat. No. 5,002,069 is gathered into the desired shape by a drawstring.

Prior art workers have devised disposable trough-forming elements made of plastic material and having a central opening. Once the surgical drape is in place, the plastic trough-foraging element is adhered to the patient's body adjacent the periphery of the fenestration of the drape. The plastic trough-forming element is provided with a fenestration of its own, or the surgeon cuts a fenestration therein suitable for the particular procedure being performed.

Copending U.S. patent application Ser. No. 08/084,001, filed Jun. 29, 1993 in the names of Veronica Ann Mills and Jeffrey L. Taylor and entitled SURGICAL DRAPE WITH IMPROVED CONSTRUCTION FOR "CRITICAL ZONE" PANEL, teaches a reusable drape having a fenestration therein. A trough-forming panel of liquid resistant material is provided with a corresponding opening, and the drape and the trough-forming panel are sewn together about the peripheries of their respective opening and fenestration. The outside edges of the trough-forming panel are then folded inwardly toward the fenestration to form trough segments. At the corners, the trough-forming panel is carefully folded and maintained in folded condition by snap means. While this system works well, it, like the other systems mentioned above, requires manipulation. If the corners are not properly folded, a direct escape channel for fluids might result. Furthermore, by virtue of the folding, the corners of the trough-forming panel are multi-layered and somewhat cumbersome.

The present invention is based upon the discovery that the problems encountered with prior art fluid collection devices can be minimized or completely eliminated. To this end, a substantially rectangular trough-forming panel of liquid resistant material is sewn to a surgical drape about the periphery of the fenestration of the surgical drape, with the trough-forming panel having an opening therein corresponding to the drape fenestration. Three or four of the outside edges of the rectangular panel are folded inwardly toward the fenestration to form trough segments. The peripheral edge of the panel at corners where adjacent trough segments meet is gathered to form smooth curved corner edges. This results in corners between adjacent trough segments which are unseamed and stitch free, unlike most prior art structures. Furthermore, the gathered corners do not require folding with consequent multi-layering. The gathered corners enable adjacent trough segments to have different depths, as will be described hereinafter.

The trough structure of the present invention requires a minimum of manipulation and is free of malleable shape forming devices, or the like. The drape and trough are easily folded and are readily cleanable by conventional washing and drying techniques and are sterilizable by any appropriate sterilization process, preferably autoclaving. The teaching of the present invention are applicable to any surgical drape for any surgical procedure in which large quantities of liquid are anticipated.

DISCLOSURE OF THE INVENTION

According to the present invention there is provided a reusable surgical drape having a liquid collecting and containment trough integral therewith. The surgical drape is provided with a fenestration positionable about the surgical site. The trough comprises a substantially rectangular panel of liquid repellant material having outwardly or convexly rounded corners. The trough-forming panel has an opening corresponding to the drape fenestration. The panel opening and the drape fenestration are aligned and the panel is sewn to the drape about the periphery of the fenestration. A binding tape is used to eliminate any rough edges about the periphery of the fenestration.

In a first embodiment of the present invention, all four sides of the trough-forming panel are folded inwardly toward the fenestration to form liquid receiving and retaining trough segments about the drape fenestration. At each of the corners where adjacent trough segments meet, the outer peripheral edge of the trough-forming panel is gathered. This results in a continuous, rectangular trough about the fenestration, having substantially rectilinear side segments and rounded corner segments free of seams, stitches, folds or multiple layers. The trough-forming panel is provided with pairs of male and female cooperating snap elements which may be used to maintain the proper shape of the trough segments assuring that they will not unfold or sag.

In a second embodiment, the drape and trough structure is substantially identical to that described above, with the exception that one of the sides of the rectangular trough-forming panel is not used to form a trough segment. The remaining three sides of the trough-forming panel are folded inwardly toward the fenestration to form trough segments with rounded, gathered corners therebetween. That side of the trough-forming panel not used to form a trough segment is sewn, along part at least of its length, to the drape. Sets of cooperating snap elements are provided to fold and close those ends of two of the trough-forming segments which are located adjacent the panel edge not used to form a trough segment.

DETAILED DESCRIPTION OF THE INVENTION

Figure 1:
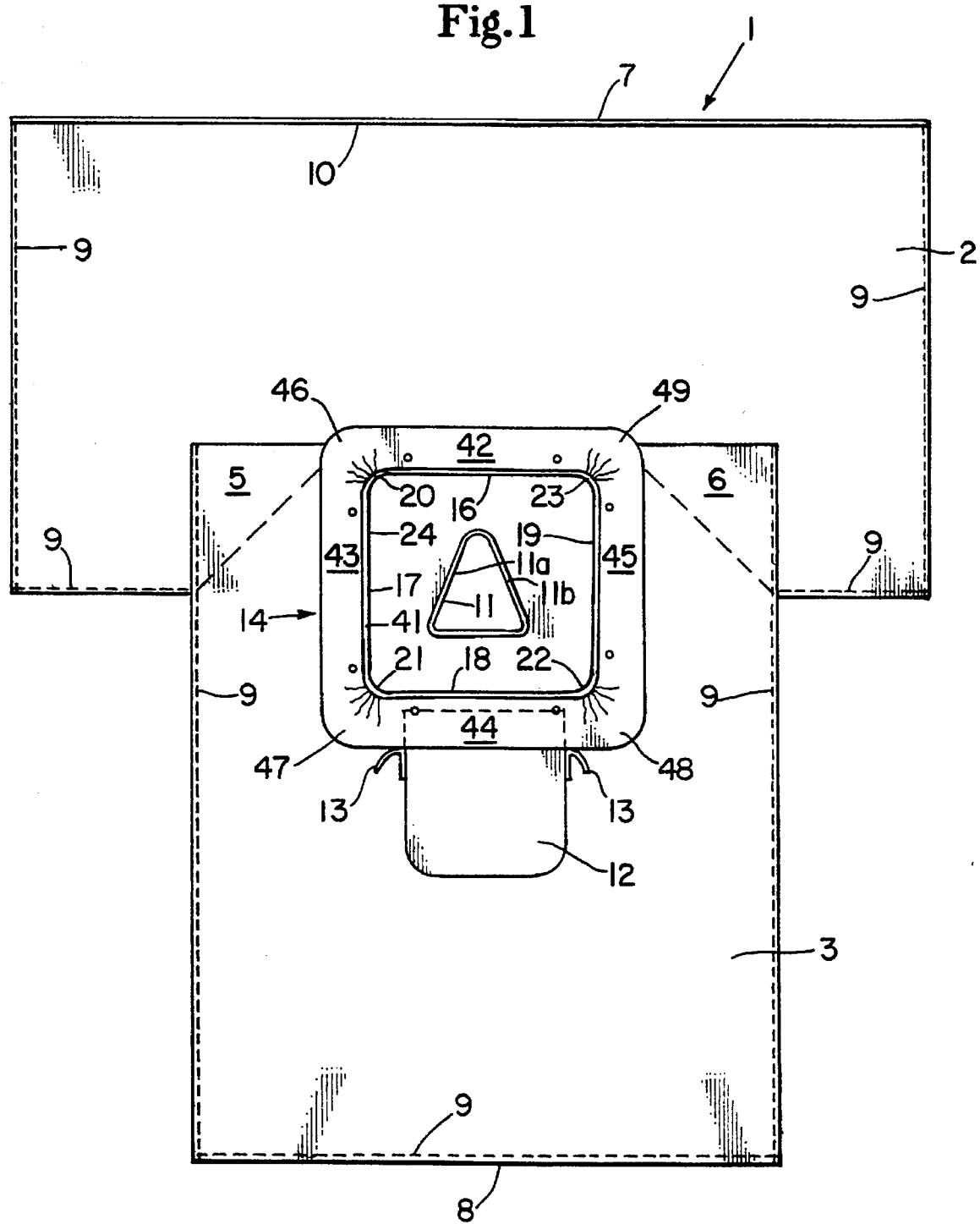
FIG. 1 is a simplified plan view of a first embodiment of a drape and trough assembly of the present invention.
Figure 2:
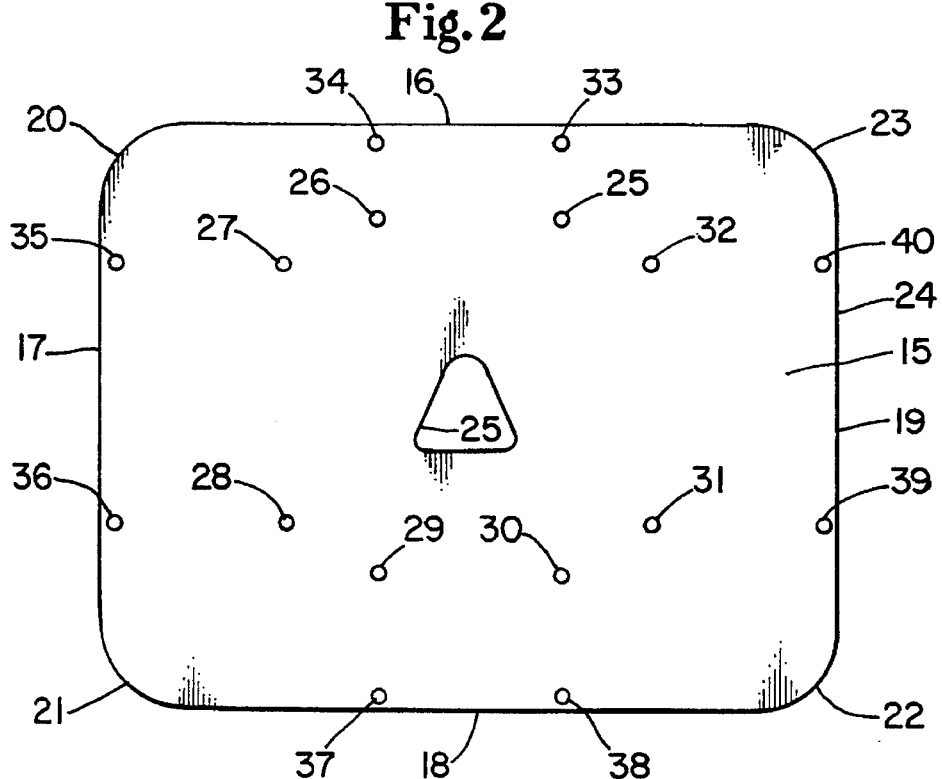
FIG. 2 is a plan view of the trough-forming panel of FIG. 1 prior to folding and prior to gathering of its corners.
Figure 3:
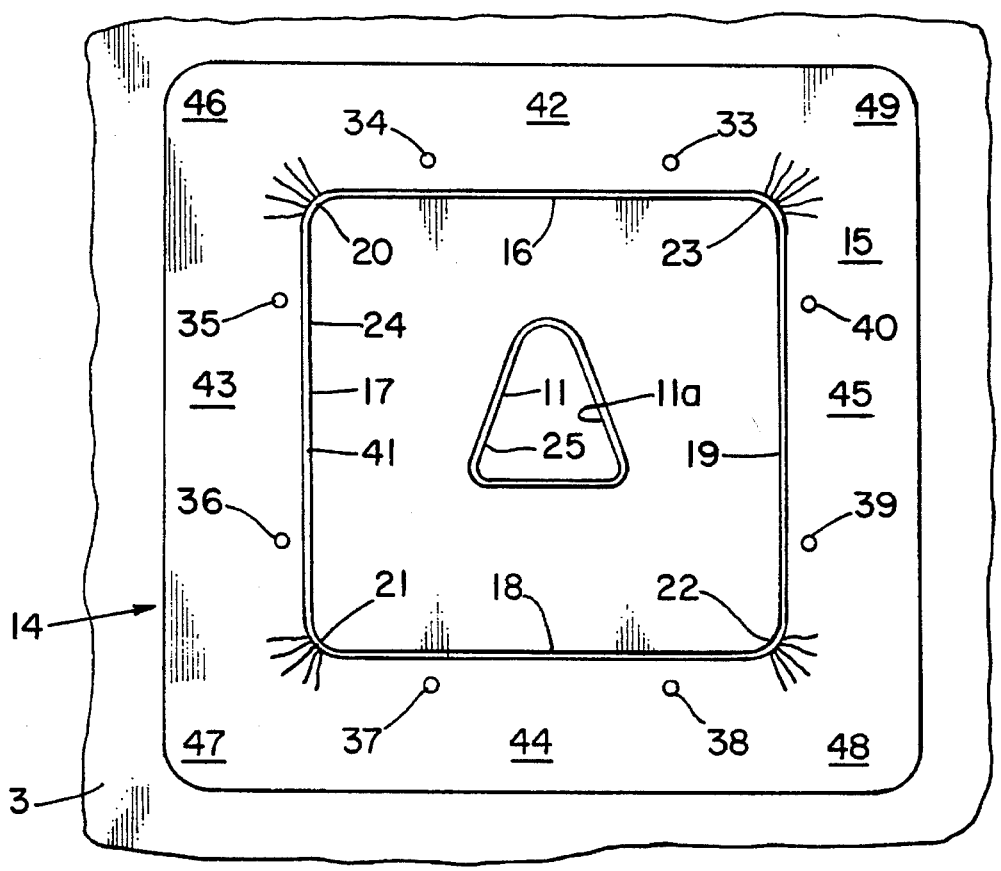
FIG. 3 is an enlarged fragmentary view of the trough of FIG. 1.

A first embodiment of the present invention is illustrated in FIGS. 1–3 wherein like parts have been given like index numerals. As indicated above, the teachings of the present invention are applicable to many different types of drapes for use with numerous types of procedures wherein large quantities of fluid will be produced at the surgical site. While not intended to be so limited, FIG. 1 is a plan view of an exemplary surgical drape of the type used during an caesarean procedure. The overall drape is generally indicated at 1 and is made up of a wing portion 2 and a body portion 3. The wing and body portions are sewn together so as to form a pair of triangular gussets 5 and 6 therebetween.

When the wing 2 and the body 3 are sewn together, the two of them constitute the base material of the surgical drape 1. The word "drape" as used herein and in the claims refers to the completed structure with all of its appurtenances.

The free transverse edge of the wing 2 defines the head end 7 of drape 1, and the free end of the body 3 constitutes the bottom end 8 of the drape. The peripheral edges of the wing 2 and body 3 are hemmed as at 9. The free transverse edge of the wing 2, defining head end 7 of the drape, may be provided with a bright color coded binding 10 for ease in folding and unfolding the drape 1. The gussets 5 and 6 enable the drape to accommodate one or both of the patient's arms in instances where one or both of the patient's arms are supported on laterally extending members.

The fabric from which the base material of the reusable drape 1 is made does not constitute a limitation of the present invention. In the particular exemplary embodiment illustrated, excellent results were achieved when the wing 2 and the body 3 were each made of single ply of a low liquid repellant fabric such as that material manufactured by Standard Textile Co. Inc. of Cincinnati, Ohio, under the mark Wrappel™.

The body 3 is provided with a fenestration 11 which is so positioned that the surgical site is exposed therethrough. While the shape of the fenestration 11 is again not a limitation of the present invention, in the particular exemplary embodiment illustrated, the fenestration 11 is substantially triangular.

The other appurtenances or the drape also do not constitute limitations of the present invention. In the particular exemplary drape illustrated, the body 3 is provided with a work area 12 spaced from fenestration 11 in the direction of the bottom end 8 of the drape 1. The work area 12 is preferably both absorbent and textured. In the particular embodiment described, excellent results were achieved when the work area 12 was made of an inner layer of liquid repellant material, such as that manufactured and sold by Standard Textile Co. Inc. of Cincinnati, Ohio, under the trademark ComPel®, and an outer layer of an absorbant, textured material, such as that manufactured and sold by Standard Textile Co. Inc. of Cincinnati, Ohio, under the mark Zorwik™. The drape may also be provided with loop-forming elements 13, each of which has cooperating male and female snap elements whereby they may be formed into a closed loop for positioning and guiding tubes, electrical wires and the like, during the procedure.

The trough of the present invention, which surrounds fenestration 11, is generally indicated at 14 in FIGS. 1 and 3. The trough 14 is made from a trough-forming panel of liquid repellant material. An example of such material suitable for this purpose is manufactured and sold by Standard Textile Co. Inc. of Cincinnati, Ohio, under the trademark ComPel®R.

The trough-forming panel is shown in FIG. 2 at 15. The liquid repellant panel 15 has rectilinear side edges 16, 17, 18 and 19 with outwardly or convexly curved corners 20, 21, 22 and 23. The rectilinear edges 16–19 and the rounded corners 20–23 form the outer peripheral edge 24.

The trough-forming panel 15 is provided with an opening 11a which preferably corresponds to the fenestration 11 in body 3, both in size and shape.

The trough-forming panel 15 is provided with a pair of female snap elements 25 and 26 inset from rectilinear edge 16, a pair of female snap elements 27 and 28 inset from edge 17, a pair of female snap elements 29 and 30 inset from edge 18 and a pair of female snap elements 31 and 32 inset from edge 19. In a similar fashion, the panel 15 is provided with a pair of male snap elements 33 and 34 adjacent edge 16, a pair of male snap elements 35 and 36 adjacent edge 18, a pair of male snap elements 37 and 38 adjacent edge 18 and a pair of male snap elements 39 and 40 adjacent edge 19. The male snap elements 33–40 are adapted to cooperate with the female snap elements 25–32, respectively, as will be evident hereinafter. The surface of the panel 15 shown in FIG. 2 will constitute the inside surface of the trough 14, once the trough 14 is formed. As a result, the sockets of female snap elements 25–32 and the plunger portions of male snap elements 33–40 face upwardly, as viewed in FIG. 2.

The trough 14 is formed by folding the rectilinear edge portions 16, 17, 18 and 19 inwardly toward the opening 11a. This is shown in FIG. 3. The corners 20–23 are each gathered and sewn forming inwardly directed or concave corners as shown in FIG. 3. The entire peripheral edge 24 has a binding tape 41 sewn thereabout to provide the trough 14 with a smooth edge, particularly at the corners 20–23. The corners 20–23 may be gathered and sewn in any appropriate manner, as for example by the use of a gathering foot on a sewing machine.

The above-noted folding and corner gathering and sewing form the trough 14 made up of trough segments 42, 43, 44 and 45 with corner segments 46, 47, 48 and 49 therebetween. Trough segment 42 faces and is substantially parallel to the head end 7 of drape 1, as is shown in FIG. 1. Similarly, the trough segment 44 faces and is substantially parallel to the bottom edge 8 of the drape I. Trough segments 43 and 45 are essentially parallel to the longitudinal edges of drape body 3. The trough 14 is attached to the body 3 of drape 1 about the corresponding edges of trough opening 11a and drape fenestration 11. The corresponding edges of the trough opening 11a and drape fenestration 11 may also be bound by a binding tape 11b, providing the fenestration with smooth edges thereabout. During a procedure, the male snap elements 33–40 may be engaged with their respective female snap elements 25–32 to maintain the shape of the trough and to prevent any of the trough segments 42–45 from sagging. The male snap elements will be disengaged from their respective female snap elements during washing and sterilization of drape 1.

From the above description and as shown in FIGS. 1 and 3, the trough segments 42–45 and the corner segments 46–49 form a continuous trough structure about fenestration 11. The trough 14 is made of a single piece of liquid repellant fabric. The trough structure 14 and particularly its corner segments 46–49 are seamless and free of stitching except about the periphery of the fenestration 11 and the outermost peripheral edge 24. Corner segments 46–49 are not folded and are not made up of folded layers. The trough 14 is extremely simple in construction and requires little or no manipulation prior to a procedure, other than the engagement of the eight male and female snap element pairs.

All of the trough segments 42–45 may have the same depth or transverse dimension. Alternatively, they may differ in depth or transverse dimension which requires only the adjustment of the corner curves during manufacture and the proper placement of the male and female snap elements.

While dimensions are not intended to constitute a limitation of the present invention, excellent results were achieved with a drape made exactly as shown in FIG. 1 wherein the maximum width of wing 2 was 108 inches, and the maximum length thereof was 60 inches. The maximum width of body 3 was 70 inches and its length was 90 inches. The overall length of the drape was 130 inches and the distance from the head end 7 to the fenestration 11 was 55 inches. The fenestration, itself, was 13 inches each side.

The overall trough structure, shown in FIGS. 1 and 3, had a width dimension of 60 inches and length dimension of 50 inches. The trough segment 42 had a transverse depth dimension of 5 inches and the trough segment 44 had a transverse depth dimension of 8 inches, while the trough segments 43 and 45 had a transverse depth dimension of 10 inches each.

To make the trough 14 of FIGS. 1 and 3, trough-forming panel 15 of FIG. 2 had an overall width from edge 17 to edge 19 of 60 inches and an overall length from edge 16 to edge 18 of 50 inches. Finally, the work area 12 had width and length dimensions of 20 inches.

Figure 4:
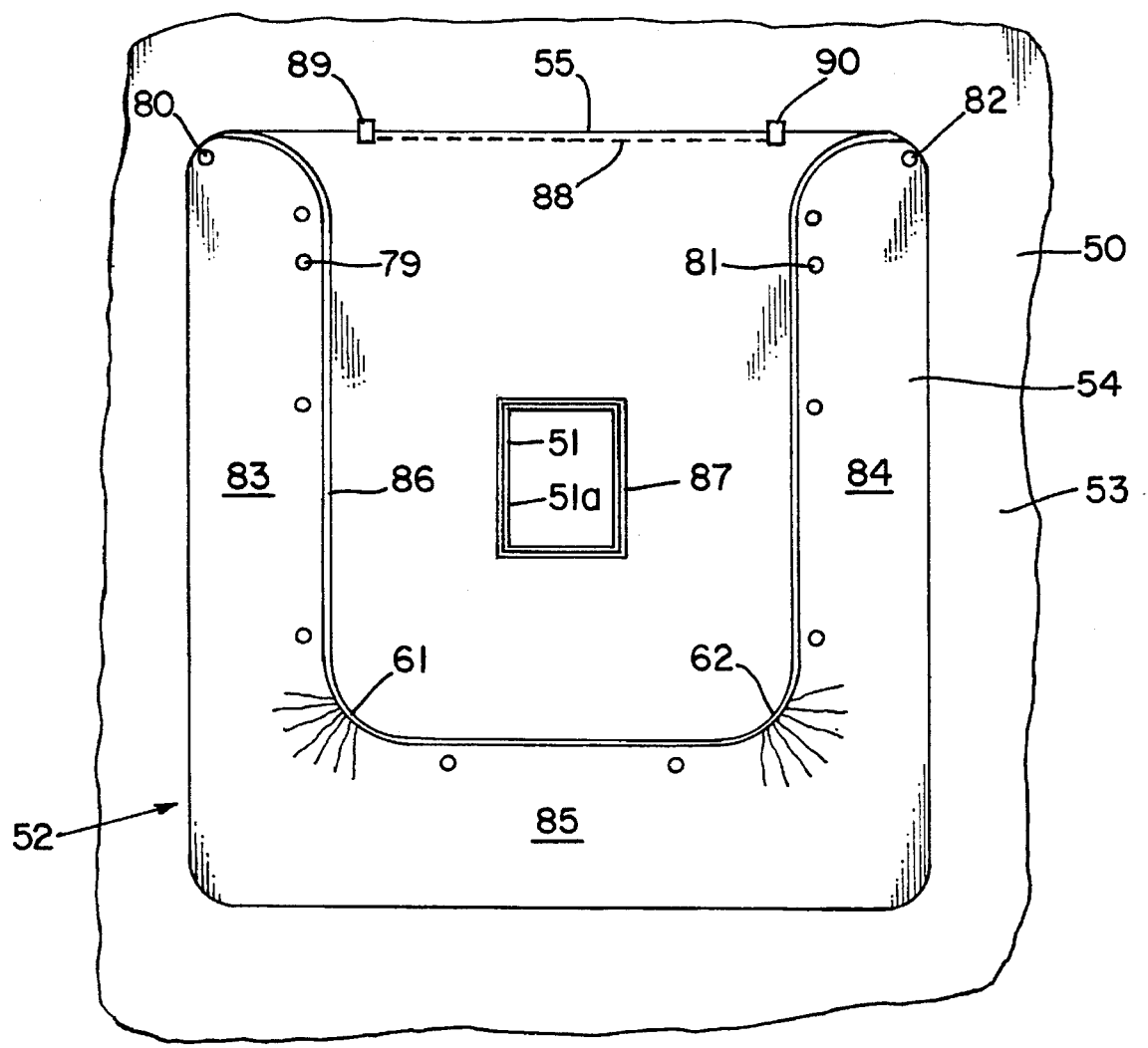
FIG. 4 is a fragmentary plan view of a second embodiment of surgical drape and trough of the present invention.

Reference is now made to FIG. 4 wherein a drape is fragmentarily shown at 50 provided with a fenestration 51 surrounded by a three-sided trough, generally indicated at 52, made in accordance with the teachings of the present invention.

There are a number of procedures which are characterized by a large liquid flow from the surgical site, but which are of such nature that containment and control of the liquid flow need only be maintained with respect to the sides and bottom of the fenestration 51. An example of such a procedure is an arthroscopic procedure and the drape 50, for purposes of an exemplary showing, may be considered to be an arthroscopic drape. The overall drape 50 may be similar in construction to that of FIG. 1 having a wing (not shown), a body (fragmentarily shown at 53) and gussets (not shown) therebetween. The wing and the body 53 of drape 50 may be made of any appropriate reusable and sterilizable material, such as the material described with respect to the wing and body of the embodiment of FIG. 1.

Figure 5:
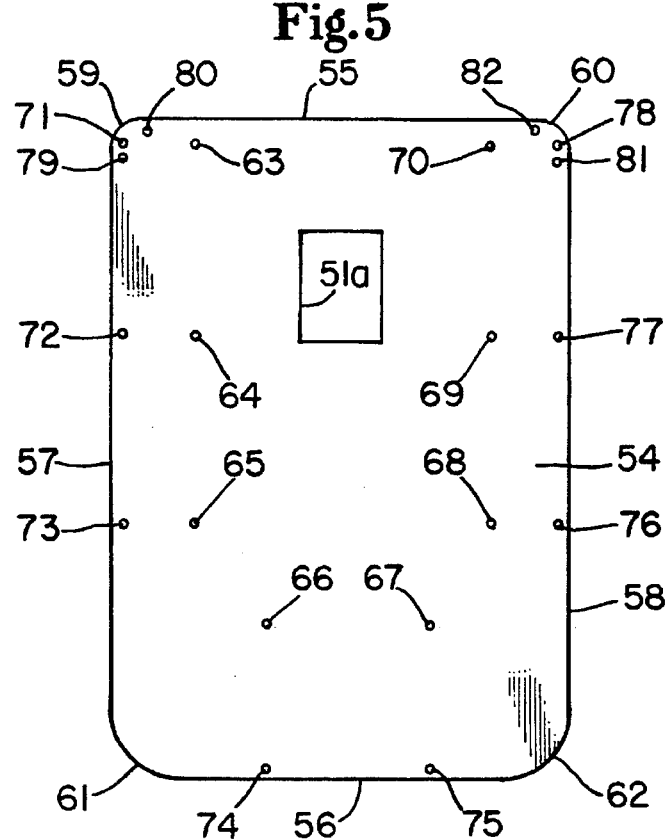
FIG. 5 is a plan view of the trough-forming panel of the embodiment of FIG. 4.

The three-sided trough 52 is made from a single panel of liquid resistant, reusable and sterilzable material such as, for example, the ComPel®R material described with respect to the trough forming panel 15 of FIG. 2. The panel from which three sided trough 52 is made is illustrated in FIG. 5 and indicated at 54. The panel 54 is substantially rectangular, having a rectilinear head end edge 55, a rectilinear foot end edge 56 and rectilinear side edges 57 and 58. The head end edge 55 terminates in shallow curved corners 59 and 60, and the foot edge 56 terminates in rounded corners 61 and 62, similar to the corners 20–23 of FIG. 2. Panel 54 is provided with an opening 51a which corresponds in size and shape to the drape fenestration 51 (see FIG. 4).

Panel 54 is provided with a plurality of female snap elements 63–70. Panel 54 is also provided with a plurality of male snap elements 71–78 which correspond to and are adapted to cooperate with female snap elements 63–70, respectively. Near corner 59, panel 54 is provided with a female snap 79 and a cooperating male snap 80. In a similar fashion, near the corner 60, the panel 54 is provided with a female snap element 81 and a cooperating male snap element 82. The purpose of female snap elements 79 and 81 and the male snap elements 80 and 82 will be apparent hereinafter. In FIG. 5 the surface of panel 54 will comprise the inside surface of three-sided trough 52. As a consequence, the sockets of female snap elements 63–70 and the plunger portions of male snap elements 71–78 face upwardly. The opposite is true of female snap elements 79 and 81 and male snap elements 80 and 82, as will be apparent hereinafter.

The side edges 57 and 58 and the foot end edge 56 are folded inwardly, as shown in FIG. 4, to form side trough segments 83 and 84 and a foot end trough segment 85. Between the trough segments 83 and 85 and 84 and 85 the corners 61 and 62 of panel 54 are gathered and sewn, as described with respect to corners 20–23 of FIG. 3. A binding tape 86 is sewn along panel edges 56, 57 and 58, corners 61 and 62 and the gently curved corners 59 and 60. The corners 61 and 62 have all of the advantages of corners 20–23 of FIG. 3, being continuous, rounded, seam-free, stitchless (except where their edges are gathered and sewn), and are not formed by folding which would result in multiple layers of the fabric.

The panel 54 is sewn to the body 53 of drape 50 about the periphery of the fenestration 51 of the drape body 53 and the corresponding opening 51a of the trough-forming panel 54. The matched edges of the fenestration 51 and the opening 51a may have a binding tape 87 sewn thereabout to prevent sharp or rough edges. The trough-forming panel 54 is also attached to the drape body 53 by being stitched as at 88 along its head end edge 55 between a pair of bartacks 89 and 90.

Figure 6:
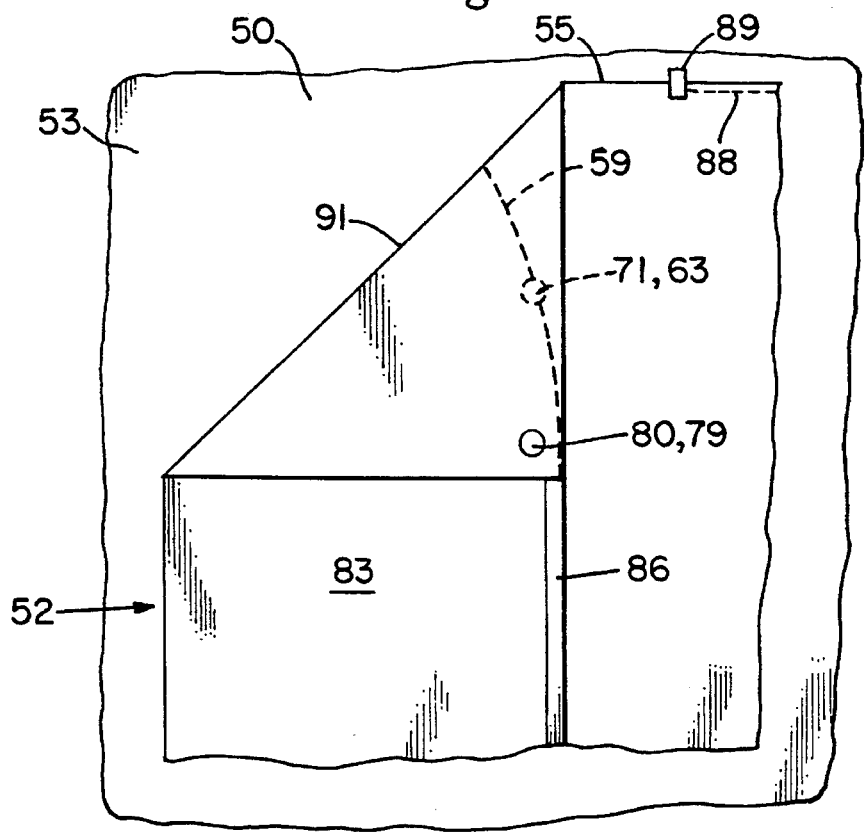
FIG. 6 is a fragmentary plan view of one of the head end corners of the trough in its folded and closed condition.

When the drape 50 is deployed upon the patient, the male snap elements 71–78 will be engaged with the female snap elements 63–70, respectively. This will maintain the proper shape of the trough elements 83, 84 and 85. The only other manipulation required with respect to the three-sided trough 52 is the closure of the free ends of trough segments 83 and 84. To this end, the male snap element 80 is caused to overly and engage the female snap element 79. As is shown in FIG. 6, this automatically folds and closes the free end of trough segment 83 as at 91. It will be understood that engagement of male snap element 82 and female snap element 81 will close the free end of trough segment 84 in an identical manner.

The drape 50, including the three sided trough 52, can be subjected to any appropriate washing and drying procedure, as well as any appropriate sterilization procedure, preferably autoclaving. Again, both the size of drape 50 and the material from which it is made do not constitute limitations of the present invention, with the exception that the three sided trough 52 (i.e. the panel 54) should be made of a liquid repellant material. In an exemplary embodiment which was made and tested, the wing (not shown) and the body (fragmentarily shown at 53) were each made of a single ply of low repellency fabric such as the above-noted Wrappel™. The panel 54 from which the three sided trough 52 was formed was made of a highly liquid repellant fabric such as the above-mentioned ComPel®R. The binding tape was made of ComPel®O, a liquid repellant fabric manufactured by the above-noted Standard Textile Co. Inc.

In the embodiment tested, the wing (not shown) had a width of 106 inches and a length of 58 inches. The drape body 53 had a width of 87 inches and a length of 88 inches. When the wing and body were sewn together, the overall drape 50 had a length of 127 inches.

The panel 54 from which the three-sided trough 52 was formed had an overall width of 47 inches and a head end edge to foot end edge length of 67 inches. When the panel 54 was formed as shown in FIG. 4, it had a width of 39 inches and a head end edge to toot end edge length of 59 inches. The side trough segments 83 and 84 had a depth of 4 inches and the foot end trough segment had a depth of 8 inches. The fenestration 51 and the corresponding opening 51a in panel 54 had a width of 9 inches and a length of 11 inches. The three-sided trough 52 was so located with respect to the overall drape 50 that the head end edge 55 of the three-sided trough 52 was located at a distance of 51 inches from the head end edge of drape 50. The fenestration 51 and corresponding opening 51a had a head end edge located 62 inches from the head end edge of the drape 50.

All of the male snap elements 71–78 and 80 and 82, together with the female snap elements 79 and 81 were located adjacent their respective edges of panel 54. The snap elements 63–65 and 68–70 were each located approximately 8 inches inwardly of their respective male snap elements 71–73 and 76–78. This assured that the side trough segments 83 and 84 had a width or depth of about 4 inches. The female snap elements 66 and 67 were located approximately 16 inches inwardly of their respective male snap elements 74 and 75 to assure that the toot end trough segment 85 had a width or depth of about 8 inches. The two male snap elements 71 and 78 were located approximately 2 inches inwardly of the head end edge 55 of panel 54. The female snap elements 79 and 81 were each located approximately 3.5 inches inwardly of head end edge 55. As is shown in FIG. 6, this arrangement assured that when the trough segment 83 was closed as by folding at 91, the snap elements 80–79 cleared the snap elements 71–63. The same, of course, would be true of snap elements 70–78 and 82–81 when the free end of trough segment 84 was closed in a similar manner.

During a procedure, when large quantities of fluid are present, a conventional suction device could be used to withdraw fluid from the trough embodiments of the present invention. Alternatively, the trough embodiments could be provided with one or more permanent tube connections so that they could be connected by tube means to an appropriate container for receipt of fluids drained from the trough embodiments. It will also be apparent to one skilled in the art that proper shaping of the panel from which the trough structure is formed, and by appropriate gathering of the peripheral edge of the panel, the trough structure could have any appropriate shape including circular, triangular, oval, obround, square or the like.

All versions of the trough structure of the present invention are washable and sterilizable. The troughs are free of folded corners, multiple layer corners, seams, and stitching (except at their peripheral edges). As a result, the trough structure is essentially leak proof. The trough structure will also catch solids, dropped instruments, or the like.

Neither embodiment of the present invention requires direct attachment to the patient. If, in a particular instance, such an attachment would be desirable, it would be possible, once the drape has been properly positioned, to provide a panel of one-side adhesive coated plastic material such as that made by 3M Medical Surgical Division of St. Paul, Minn., under the mark Steri-Drape™2. The plastic panel would be cut so as to have a peripheral edge corresponding to but slightly larger than the peripheral edge of the drape fenestration. The plastic panel would be provided with an opening having a shape generally corresponding to that of the fenestration, but of slightly smaller dimensions. The plastic panel, so prepared, would be applied both to the patient's skin about the surgical site, and to the trough-like structure adjacent the drape fenestration.

Modifications may be made in the invention without departing from the spirit of it.

We claim:

1. A fabric reusable and sterilizable surgical drape having a surgical site fenestration with a fluid-retaining trough extending at least partway thereabout, said trough comprising a panel of fluid-repellant fabric having an opening formed therein corresponding in size and shape to said drape fenestration and aligned therewith, said panel being attached to said drape about the peripheries of said panel opening and said drape fenestration, a part at least of the peripheral edge of said panel being folded inwardly toward said fenestration to form said trough, said trough having at least one portion wherein said trough is curved, said inwardly folded peripheral edge portion being gathered at said at least one curved trough portion, said trough being free of seams, folds, and multiple folded layers.

2. The surgical drape claimed in claim 1 including a binding tape finishing said inwardly folded peripheral edge portion of said panel.

3. The surgical drape claimed in claim 1 wherein said trough completely surrounds said fenestration.

4. The surgical drape claimed in claim 1 including means to cause said trough to maintain its shape.

5. The surgical drape claimed in claim 1 wherein said trough is continuous, rectangular and completely surrounds said fenestration, said trough comprising four rectilinear segments with curved and gathered corners between adjacent segments.

6. The surgical drape claimed in claim 1 wherein said trough is U-shaped about said fenestration, comprising three rectilinear segments joined by two curved and gathered corners.

7. The surgical drape claimed in claim 5 including cooperating male and female snap means on said panel and so positioned thereon as to maintain the shape of said trough segments.

8. The surgical drape claimed in claim 5 wherein at least one trough segment has a depth dimension different from said other trough segments.

9. The surgical drape claimed in claim 5 wherein said drape has a head end, a bottom end and side edges, said trough having one segment parallel to said drape head end, one segment parallel to said drape bottom end, and two segments parallel to said drape side edges.

10. The surgical drape claimed in claim 6 including cooperating male and female snap means on said panel and so positioned thereon as to maintain the shape of said trough segments.

11. The surgical drape claimed in claim 6 wherein at least one trough segment has a depth dimension different from said other trough segments.

12. The surgical drape claimed in claim 6 wherein said drape has a head end, a bottom end, and side edges, said trough having one segment parallel to said drape bottom end and two segments parallel to said drape side edges.

13. The surgical drape claimed in claim 12 wherein said trough segments parallel to said drape side edges have ends facing said drape bottom end connected by said curved and gathered corners to said segment parallel to said drape bottom end, said trough segments parallel to said drape side edges having ends facing said drape head end which are folded into a closed condition and maintained in said closed condition by cooperating male and female snap means on said panel, said panel having an unfolded peripheral edge portion parallel to said drape head end and sewn along at least a part of its length to said drape.

* * * * *